United States Patent [19]

Kuiterman et al.

[11] Patent Number: 5,728,892
[45] Date of Patent: Mar. 17, 1998

[54] METHOD FOR PREPARING AN ALPHA-ALKYCINNAMALDEHYDE

[75] Inventors: Alie Kuiterman, Sittard; Hubertus J. A. Dielemans, Beek; Richard Green, Geleen; Anna M. C. F. Castelijns, Beek, all of Netherlands

[73] Assignee: DSM N.V., Heerlen, Netherlands

[21] Appl. No.: 746,162

[22] Filed: Nov. 6, 1996

[30] Foreign Application Priority Data

Nov. 6, 1995 [BE] Belgium ................. 9500910

[51] Int. Cl.$^6$ ........................................ C07C 45/00
[52] U.S. Cl. ........................................... 568/433
[58] Field of Search ............................... 568/433

[56] References Cited

U.S. PATENT DOCUMENTS 4,920,232  4/1990  Goetz et al. .
5,214,151  5/1993  Nakajima et al. .

FOREIGN PATENT DOCUMENTS

| 0 298 380 A3 | 7/1988 | European Pat. Off. . |
| 0 298 380 A2 | 1/1989 | European Pat. Off. . |
| 2201280 | 10/1973 | France . |
| 506850 | 7/1939 | Germany . |
| 91/07371 | 5/1991 | WIPO . |

*Primary Examiner*—Samuel Barts
*Attorney, Agent, or Firm*—Cushman Darby & Cushman IP Group of Pillsbury Madison & Sutro, LLP

[57] ABSTRACT

The invention relates to a method for preparing an α-alkylcinnamaldehyde via aldol concensation of a benzaldehyde and an alkanal, with pyrrolidine being employed as a catalyst. The method is suitable, in particular, for preparing α-hexylcinnamaldehyde by aldol condensation of benzaldehyde and n-octanal, in particular for preparing α-hexylcinnamaldehyde of olfactory quality, since it was found that, in the method according to the invention, relatively little α-hexyldecenal, the aldol condensation product of n-octanal, is formed. Preferably, the aldol condensation is carried out without a solvent in the presence of an acid, and the alkanal is metered in over time to a mixture which contains pyrrolidine and benzaldehyde.

14 Claims, No Drawings

METHOD FOR PREPARING AN ALPHA-ALKYCINNAMALDEHYDE

BACKGROUND OF THE INVENTION

1. Field of the Invention

The invention relates to a method for preparing an α-alkylcinnamaldehyde via aldol condensation of a benzaldehyde and an alkanal in the presence of a base as a catalyst.

It is known to prepare α-alkylcinnamaldehydes via aldol condensation of a benzaldehyde and an alkanal in the presence of an alkali metal hydroxide or an alkali metal carbonate as the base, in highly dilute reaction media, the solvent employed comprising alcohols, for example methanol, ethanol or glycols.

2. Background of the Art

EP-A-392579 describes, for example, the preparation of α-hexylcinnamaldehyde from benzaldehyde and octanal, potassium hydroxide being employed as the catalyst and glycol being employed as the solvent.

A drawback of the known method is that the selectivity with respect to, in particular, benzaldehyde is relatively low. Moreover, since a large quantity of solvent has to be employed, the production capacity is relatively low.

SUMMARY OF THE INVENTION

The object of the invention is to provide a method wherein α-alkylcinnamaldehydes can be prepared with a high selectivity with respect to benzaldehyde and alkanal employed, and by means of which a high production capacity can be accomplished. This is achieved, according to the invention, by employing pyrrolidine as the catalyst.

This is because, surprisingly, it was found that as a result of pyrrolidine being employed as the catalyst, it is possible to achieve a high selectivity with respect to benzaldehyde and alkanal, whereas the use of other amines resulted in much lower selectivities.

Additionally it was found that the reaction proceeds smoothly without a solvent, an increased production capacity being accomplished as a result. An attendant advantage, moreover, is that the reaction mixture can be worked up in a simple manner. By preference, therefore, the reaction is carried out in the absence of a solvent.

DETAILED DESCRIPTION

The method according to the invention can employ, as an alkanal, for example an aldehyde of the formula $R-CH_2-CHO$, where R preferably represents an alkyl group having 4–10 C atoms, in particular 6–7 C atoms. The benzaldehyde may or may not be substituted in the nucleus by groups which are inert during the aldol condensation.

The ratio of benzaldehyde to be employed to alkanal is not particularly critical. Owing to the generally high tendency of the alkanal to be reactive and the concomitant self-condensation of the alkanal, an excess of benzaldehyde with respect to alkanal is generally employed. Preferably, a molar ratio of benzaldehyde to alkanal of between 1.0 and 2.5, in particular between 1.2 and 1.8, is employed. Preferably, the alkanal is metered in over time to a reaction mixture which contains benzaldehyde and pyrrolidine.

The method according to the invention is suitable, in particular, for preparing α-hexylcinnamaldehyde by aldol condensation of benzaldehyde and n-octanal, in particular for preparing α-hexylcinnamaldehyde of olfactory quality. As a matter of fact, it was found that, in the aldol condensation of benzaldehyde and octanal with pyrrolidine as catalyst, relatively little α-hexyl-decenal, the aldol condensation product of octanal, is formed. α-Hexyldecenal cannot easily be separated by distillation from α-hexylcinnamaldehyde and has an adverse effect on the quality of the odor.

The temperature at which the aldol condensation is carried out is not critical and is in practice often between 50° and 100° C., preferably between 75° and 95° C., in particular between 80° and 90° C.

The amount of pyrrolidine employed in the aldol condensation can vary within wide limits and is preferably between 0.05 and 0.5 molar equivalent, calculated on the basis of the amount of alkanal employed, in particular between 0.07 and 0.20 molar equivalent. The best results in the preparation of α-hexylcinnamaldehyde were achieved with 0.12–0.15 molar equivalent of pyrrolidine on the basis of the amount of octanal employed.

During the aldol condensation a quantity of an acid is preferably also present. This is because it was found that the selectivity can thereby be increased even further. Suitable acids are, for example, carboxylic acids, in particular acetic acid and/or octanoic acid, mineral acids, in particular sulphuric acid or hydrochloric acid, or organic acids, for example p-toluenesulphonic acid. The quantity of acid is preferably more than 0.05 milliequivalent of acid per gram of alkanal, in particular 0.1–1 milliequivalent of acid per gram of alkanal.

From the reaction mixture obtained after the aldol condensation it is then possible, in a simple manner, to isolate the α-alkylcinnamaldehyde, of olfactory quality if desired, for example by washing the crude reaction mixture with an NaOH solution and neutralizing with acid, followed by phase separation, after which the organic phase is distilled, benzaldehyde being liberated in the process which can be recycled to the aldol condensation, and the main fraction, which mainly consists of the α-alkylcinnamaldehyde, being isolated or, if required, once more being subjected to distillation, in order to obtain α-alkylcinnamaldehyde of olfactory quality.

The method according to the invention can be implemented either as a batch or as a continuous process.

The invention will now be explained in more detail with reference to the following examples without, however, being limited thereto.

EXAMPLES

Example I

A double-walled glass reactor having a volume of 0.25 litre, which was provided with a turbine stirrer, water cooler, metering line and thermocouple, was successively charged with: 91.8 grams of benzaldehyde (0.86 mol), 6.15 grams of pyrrolidine (0.086 mol) and 0.15 gram of diphenylamine (as a stabilizer). The contents of the reactor were then heated, with the aid of an oil thermostat, to 85° C. From a reservoir, n-octanal was then metered in, below the liquid surface, with the aid of a metering pump. In total, 74.8 grams of octanal (0.58 mol), whose acid level had been set, with the aid of acetic acid, to 0.25 meq/g of octanal, are metered in over 3 hours. After the octanal had been metered in, the reaction was allowed to continue for a further 15 minutes, and the contents were then cooled down to room temperature and analysed with the aid of GLC.

The conversion of the benzaldehyde (bald) amounted to 65.6% and the degree of conversion of octanal to 100%. The selectivities of benzaldehyde and octanal to give α-hexylcinnamaldehyde (α-hex) were 94.9% and 96.2%, respectively, while the selectivity of octanal to give α-hexyldecenal (α-HD) was 1.0%.

Comparative experiments A to E inclusive

In a similar manner as described in Example I, the experiments listed below were carried out, except that pyrrolidine as the catalyst was replaced by piperidine, diethylamine, n-propylamine, triethylamine and d,l-phenylalanine, respectively. The results are represented in Table 1.

TABLE 1

| Amine | Conv. octanal % | Conv. bald. % | Sel. α-hex with respect to octanal % | Sel. α-HD with respect to octanal % | Sum sel. with respect to octanal % | Sel. α-hex with respect to bald. % |
| --- | --- | --- | --- | --- | --- | --- |
| Piperidine | 84.2 | 29.3 | 45.1 | 32.3 | 77.4 | 84.3 |
| Diethylamine | 68.9 | 14.0 | 12.0 | 44.0 | 56.0 | 38.4 |
| n-Propylamine | 68.6 | 18.3 | 40.2 | 7.4 | 47.6 | 97.5 |
| Triethylamine | 2.0 | 1.2 | 0.0 | 35.3 | 35.3 | 0.0 |
| Phenylalanine | 75.0 | 18.8 | 21.1 | 58.2 | 79.3 | 55.7 |

Example II

The reaction was carried out in a 2.5 litre double-walled glass reactor provided with a cooler, turbine stirrer (6 blades), thermocouple and a submerged metering tube. A mixture of 1065 grams of benzaldehyde (10.0 mol), 48.8 grams of pyrrolidine (0.679 mol) and 1.8 grams of diphenylamine was heated to 85° C. Over a period of 180 minutes, 878 grams of acidified (0.34 meq/gram) octanal (6.648 mol) were metered in at 85° C. Acidification of the octanal was effected with 16.9 grams of acetic acid (0.281 mol). The reaction was allowed to continue at 85° C. for a further 15 minutes. The reaction mixture was cooled to 65° C. and washed at 50° C., for 15 minutes, with 500.3 grams of 5% strength aqueous NaOH solution (0.625 mol). After neutralization with 78 grams of acetic acid (1.30 mol) for 15 minutes at 50° C., the reaction mixture was separated at 50° C., over a period of 5 to 6 minutes. The organic layer (1869.8 grams) contained 25.5% of benzaldehyde, 2.1% of octanal, 59.8% of α-hexylcinnamaldehyde and 4.6% of α-hexyldecenal. The degrees of conversion of benzaldehyde and octanal were 55.2% and 95.5%, respectively. The selectivity in producing α-hexylcinnamaldehyde was 93.5% with respect to benzaldehyde and 81.4% with respect to octanal.

Example III

The reaction was carried out in the same reactor and by the same method as in Example II. A mixture of 1065 grams of benzaldehyde (10.0 mol), 73 grams of pyrrolidine (1.02 mol) and 1.8 grams of diphenylamine was heated to 85° C. Over a period of 180 minutes, 875 grams of acidified (0.20 meq/gram) octanal (6.69 mol) were metered in at 85° C. The reaction mixture was cooled to 65° C. and washed at 50° C., for 15 minutes, with 970 grams of 0.76M aqueous Na$_2$CO$_3$ solution. After neutralization with 100 grams of acetic acid (1.68 mol), the reaction mixture was separated at 50° C., over a period of 15 minutes. The organic layer (1864 grams) contained 19.9% of benzaldehyde, 0.3% of octanal, 72.6% of α-hexylcinnamaldehyde and 0.7% of α-hexyldecenal. The degrees of conversion of benzaldehyde and octanal were 65.0% and 99.4%, respectively. The selectivity producing α-hexylcinnamaldehyde was 95.9% with respect to benzaldehyde and 94.1% with respect to octanal.

Example IV

The reaction was carried out in a 30 litre reactor (D=300 mm), provided with an open turbine stirrer (D=100 mm) and a submerged metering tube which is positioned next to the stirrer blades. The reactor was inerted with the aid of N$_2$ and preheated to 60° C. 8300 grams of benzaldehyde (78.1 mol), 561 grams of pyrrolidine (7.8 mol) and 16 grams of diphenylamine were metered into the reactor and then heated to 85° C. Over a period of 180 minutes, 6745 grams of octanal (52.1 mol), admixed with 81 grams of acetic acid (1.35 mol), were metered in at 85° C. The reaction was allowed to continue at 85° C. for a further 15 minutes.

After the reactor contents had been cooled to 65° C., 3930 grams of 5% strength aqueous NaOH solution were added and the mixture stirred for 15 minutes at 50° C. The reaction mixture was then neutralized with 790 grams of acetic acid (13.0 mol) and stirred for 15 minutes at 50° C.–55° C. After a separation at 50° C. for 15 minutes, the organic phase (14.2 kilograms) was distilled. The organic phase contained 19.1% of benzaldehyde, 0.2% of octanal, 75.0% of α-hexylcinnamaldehyde and 0.5% of α-hexyldecenal.

The organic phase was distilled under reduced pressure (p=5–10 mbar). After the lights had been removed, the excess of benzaldehyde was distilled off; this can be recycled into the preparation. After a small intermediate fraction had been removed, α-hexylcinnamaldehyde was then isolated as the main fraction having a purity of >98%. Redistillation of this main fraction under reduced pressure (p=5–10 mbar) afforded, after separation of a small amount of forerun, a main fraction of α-hexylcinnamaldehyde of olfactory quality and a purity >99%.

What is claimed is:

1. A method for preparing an α-alkylcinnamaldehyde comprising effecting aldol condensation of a benzaldehyde and an alkanal in the presence of a base as a catalyst, wherein the catalyst is pyrrolidine.

2. The method of claim 1, wherein an alkanal of the formula R—CH$_2$—CHO is employed, where R represents an alkyl group having 4–10 C atoms.

3. The method of claim 1 or 2, wherein α-hexylcinnamaldehyde is prepared via aldol condensation of benzaldehyde and n-octanal.

4. The method of claim 1, wherein during the aldol condensation, an acid is also present in the reaction mixture.

5. The method of claim 4, wherein the acid is octanoic acid and/or acetic acid.

6. The method of claim 1, wherein the aldol condensation is carried out in the absence of a solvent.

7. The method of claim 1, wherein the aldol condensation is carried out at a temperature of between 80° and 90° C.

8. The method of claim 1, wherein a molar ratio of benzaldehyde to alkanal is between 1.2 and 1.8.

9. The method of claim 1, wherein the alkanal is metered in over time to a reaction mixture which contains the benzaldehyde and the pyrrolidine.

10. The method of claim 1, further comprising the step of isolating the α-aklylcinnamaldehyde.

11. The method of claim 10, further comprising the steps of subjecting the isolated α-aklylcinnamaldehyde to distillation.

12. The method of claim 1, wherein said method is carried out continuously.

13. The method of claim 1, wherein said method is carried out in a batch method.

14. The method of claim 1, wherein the catalyst is in an amount of 0.05 to 0.5 molar equivalent calculated on the basis of an amount of the alkanal.

* * * * *